United States Patent [19]

Yamamoto et al.

[11] Patent Number: 4,728,721

[45] Date of Patent: Mar. 1, 1988

[54] POLYMER, PRODUCTION AND USE THEREOF

[75] Inventors: Masaki Yamamoto; Hiroaki Okada; Yasuaki Ogawa, all of Osaka; Tsutomu Miyagawa, Saitama, all of Japan

[73] Assignees: Takeda Chemical Industries, Ltd.; Wako Pure Chemical Industries, Ltd., both of Osaka, Japan

[21] Appl. No.: 858,040

[22] Filed: May 1, 1986

[30] Foreign Application Priority Data

May 7, 1985 [JP] Japan .................................. 60-97617

[51] Int. Cl.$^4$ ............................................. C08G 63/74
[52] U.S. Cl. .................................... 528/361; 528/354; 528/499
[58] Field of Search ......................... 528/354, 361, 499

[56] References Cited

U.S. PATENT DOCUMENTS

| 3,297,033 | 1/1967 | Schmitt et al. | 528/361 X |
| 3,565,869 | 2/1971 | De Prospero | 528/361 X |
| 3,839,297 | 10/1974 | Wasserman et al. | 528/354 X |
| 3,890,283 | 6/1975 | Casey et al. | 528/503 X |
| 4,273,920 | 6/1981 | Nevin | 528/361 |
| 4,605,730 | 8/1986 | Shalaby et al. | 525/415 X |

OTHER PUBLICATIONS

Colin G. Pitt, et al. "Sustained Drug Delivery Systems". I. The Permeability of Poly(eta-Caprolactone), Poly (DL-Lactic Acid), and Their Copolymers, *Journal of Biomedical Materials Research*, vol. 13, pp. 498–507 (1979).

*Primary Examiner*—Earl Nielsen
*Attorney, Agent, or Firm*—Wegner & Bretschneider

[57] ABSTRACT

The present invention provides a biodegradable high molecular polymer characterized in that the content of water-soluble low molecular compounds, as calculated on the assumption that said compounds each is a monobasic acid, is less than 0.01 mole per 100 grams of said high molecular polymer.

The thus-obtained molecular polymer has good aging stability and can be used advantageously as an excipient for pharmaceutical preparations.

11 Claims, 1 Drawing Figure

POLYMER, PRODUCTION AND USE THEREOF

This invention relates to a biodegradable (degradable in vivo) high molecular polymer useful as an excipient in producing pharmaceutical preparations and a method of producing the same.

Biodegradable high molecular polymers may be used, for example, as excipients for pharmaceutical preparations such as microcapsules. As examples of such biodegradable high molecular polymers, copolymers of lactic acid and glycolic acid are known to be obtainable by polycondensation of lactic acid and glycolic acid in the presence of a strongly acidic ion exchange resin (cf. U.S. Pat. No. 4,273,920).

The present inventors also established that polymers or copolymers of lactic acid and/or glycolic acid may be obtained by polycondensation in the presence of a solid inorganic acid catalyst or by polycondensation without catalyst followed by removal of water and then polycondensation (cf. EPC Patent Publication (laid open) No. 0171907).

When produced by the methods so far used, biodegradable high molecular polymers contain low molecular compounds such as an unreacted monomer or monomers and polymers of low polymerization degree, so that when they are used in producing microcapsules, incorporation rates into microcapsules of drugs to be microencapsulated are decreased or the so-called initial burst, namely extraordinarily initial drug release from microcapsules after administration, tends to increase.

Furthermore, biodegradable high molecular polymers are chemically unstable. When allowed to stand at room temperature for several weeks to several months, they undergo degradation, which result in decrease in polymerization degree.

In view of the above drawbacks, the present inventors treated said biodegradable high molecular polymers by a variety of methods and, as a result, it was found that the content of water-soluble low molecular compounds may be reduced by treating said polymers with water or a mixture of water and an organic solvent readily soluble in water. Further investigation based on this finding has now led to completion of the present invention.

Thus, the invention provides a biodegradable high molecular polymer characterized in that the content of water-soluble low molecular compounds as calculated on the assumption that said compounds each are a monobasic acid is less than 0.01 mole per 100 grams of said high molecular polymer, a method of producing the biodegradable high molecular polymer which method comprises removing water-soluble low molecular compounds from a biodegradable high molecular polymer containing not less than 0.01 mole of water-soluble low molecular compounds per 100 grams thereof (as calculated on the assumption that said compounds each is a monobasic acid) using water or a mixture of water and an organic solvent readily soluble in water, a microcapsule for injectable sustained release containing ingredient and the biodegradable high molecular polymer, and producing the same.

The biodegradable high molecular polymer to serve as the starting material in performing the method of the invention may be produced by any method, for example by the method described in the above-cited U.S. Pat. No. 4,273,920 and EPC Patent Publication (laid open) No. 01719067.

Said starting material contains water-soluble low molecular compounds in an amount of not less than 0.01 mole per 100 grams thereof as calculated on the assumption that each of said compounds is a monobasic acid.

The content of water-soluble low molecular compounds may be determined by ordinary neutralization titration. Thus, for example, 300 mg of a starting high molecular compound is dissolved in 10 ml of dichloromethane, the solution is stirred and shaken with 20 ml of distilled water for 10 minutes, the mixture is separated into an aqueous phase and an oily phase using a centrifuge, and the aqueous phase is assayed for free acids by neutralization titration using N/100 aqueous NaOH solution with phenolphthalein as an indicator. The number of moles of NaOH required for neutralization is converted to a free monobasic acid content.

The biodegradable high molecular polymer according to the present invention preferably has good biocompatibility and thus includes, among others, hydroxy acid polyesters (e.g. polylactic acid, polyhydroxybutyric acid, poly-$\gamma$-caprolactone, polyorthoesters and polyorthocarbonates.

Said high molecular polymer may be a copolymer produced by using two or more different monomers as the monomers for forming said high molecular polymer. Said high molecular polymer may also be a block polymer or a graft polymer.

Among the high molecular polymers mentioned above, those degradable in vivo at relatively high degradation rates are preferred.

Preferred examples of the high molecular polymer according to the present invention are polylactic acid and copolymers of lactic acid and glycolic acid. As the copolymers of lactic acid and glycolic acid, mention may be made of those comprising about 100–50 mole percent of lactic acid with the balance being glycolic acid.

Furthermore, those copolymers of lactic acid and glycolic acid which have a weight average molecular weight of about 2,000–50,000 are preferred.

Further mention may be made of those copolymers of lactic acid and glycolic acid which are composed of about 90–50 mole percent of lactic acid and about 10–50 mole percent of glycolic acid and have a weight average molecular weight of about 5,000–35,000 and an inherent viscosity of about 0.05–0.5 dl/g as determined with a 0.5 weight percent chloroform solution thereof.

Examples of the organic solvent readily soluble in water which are suited for use in carrying out the method of the present invention are acetone, methanol, ethanol, tetrahydrofuran, acetonitrile and ethyl acetate. Among these, preferred from the safety viewpoint are acetone and ethanol, and ethanol is more preferred.

When a mixture of water and such readily water-soluble organic solvent is used, the water/organic solvent ratio (v/v) may be within the range of about 100/0 to 100/100, especially 100% water.

In carrying out the method of the invention, high molecular polymer as the raw material is preferably dissolved in 3 to 20 time the amount (w/v) of an organic solvent [e.g. halogenated alkane (e.g. dichloromethane, chloroform, dichloroethane, trichloroethane), acetone, tetrahydrofuran, ethyl acetate, benzene] in advance to treatment by said method since the use thereof in solution form is more efficient, although it may be used also in solid form (e.g. powder). Thus, when brought into contact with water or a mixture of water and an organic solvent readily soluble in water, such high molecular polymerization product dissolved in an organic solvent may acquire a markedly increased contact surface area upon application of stirring or some other appropriate means.

The method according to the invention is conducted generally at a temperature of about 0°–90° C., preferably about 20°–70° C.

In accordance with the present invention, the biodegradable high molecular polymerization product serving as raw material is mixed with water or a mixture of water and an organic solvent readily soluble in water with stirring to thereby remove water-soluble low molecular compounds as a result of dissolution thereof in water or said mixture. Since the desired biodegradable high molecular polymer is insoluble in water or said mixture said low molecular compounds may be separated from the desired high molecular polymer.

Although the ratio in quantity between water or a mixture of water and an organic solvent readily soluble in water and the high molecular polymerization product serving as raw material is not critical for the method according to the invention, it is desirable that water or the mixture should be used in large excess. The treatment may also be carried out in a system equipped with an appropriate collecting means and suited for continuous rinsing with water.

The above-mentioned stirring of water or the mixture may be effected by means of any of ordinary stirrers, shakers, blenders and the like. Means highly capable of causing sufficient mixing to remove unreacted material or materials and water-soluble low molecular compounds from said high molecular polymer to a satisfactory extent are desirable.

Since the desired high molecular polymer is not dissolved in water or said mixture but precipitates or separates, it may be recovered by separating the precipitate, liquid droplets or solids by, for example, filtration or the like, and then drying the same.

By carrying out the method according to the invention, water-soluble low molecular compounds may be eliminated from the raw high molecular polymerization product with good efficiency.

In purifying high molecular polymerization products in general, the primary object is to remove catalysts, gaseous monomers, or highly toxic monomers (e.g. vinyl chloride). In some instances, removal of low molecular compounds and/or unreacted materials is also intended, as in the present invention. In such instances, the distillation method is mostly employed to thereby remove initial boiling fractions. However, removal of trace amounts of water-soluble substances is generally unnecessary and, as a general rule, such method of removing trace amount of water-soluble substances as provided by the present invention is thought unnecessary and is not in practice.

The biodegradable high molecular polymer thus obtained has the following features:

(1) The high molecular polymer obtained by the method of the present invention as such or in pharmaceutical preparations produced by using said high molecular polymer shows good stability in aging.

(2) When microcapsules are produced by using the high molecular polymer obtained by the method of the present invention in w/o/w emulsion formation, followed by in-water drying, increased rates of drug incorporation in said microencapsulation are obtained.

(3) When microcapsules are produced by the method mentioned above in (2) using the high molecular polymer obtained by the method of the present invention, the initial burst (release by one day) of drugs from microcapsules is markedly reduced, so that the drugs are constantly released over a prolonged period of time.

The biodegradable high molecular polymer obtained by the method of the present invention may be used, for instance, as an excipient for microcapsules. Thus, for example, sustained release microcapsules containing a water-soluble ingredient, e.g. peptides, such as those having luteinizing hormone releasing hormone-like activity and thyroid hormone releasing hormone-like activity, may be produced by preparing a w/o emulsion with a solution containing a water-soluble ingredient serving as the inner water phase, with a drug-retaining substance (most preferably gelatin, albumin, pectin, agar, or the like) added to the inner water phase as desired, and a solution containing the biodegradable high molecular polymer obtained by the method of the invention serving as the oil phase, dispersing said emulsiuon in a water phase to give a w/o/w emulsion (preferbly adjusting the viscosity of the w/o emulsion for preparing said w/o/w emulsion to about 150–10,000 cp), and subjecting the latter emulsion to a third aqueous layer to give a w/o/w ternary layer emulsion and then the solvent in oil layer is desorbed. The thus-obtained microcapsules may be administered as a sustained release injection. The dose of such microcapsules may vary depending on the kind and content of the water-soluble active ingredient, the dosage form, the duration of drug release, the animal to be treated (e.g. warm-blooded mammal such as mouse, rat, horse, cattle or human) and the object of administration. In any case, a dose is sufficient if it corresponds to the effective amount of said active ingredient. For instance, the dose may be suitably selected within the range of about 0.02–200 mg/kg, preferably about 0.2–40 mg/kg, of microcapsules per administration. In the use in a suspension form for the above-mentioned administration as an injection, the dose may be suitably selected within the range of about 0.1–5 ml, preferably about 0.5–3 ml, of the suspension.

EXAMPLES

Figure 1:
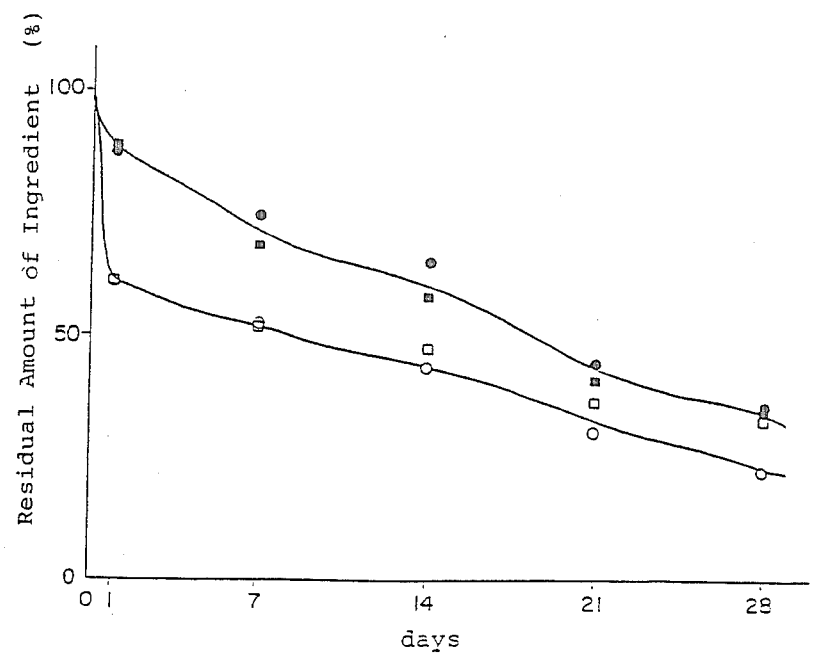
FIG. 1 represents the changes with time in residual drug content in the microcapsules obtained in Reference Example 3.

The following reference examples and working examples illustrate the invention in further detail.

REFERENCE EXAMPLE 1

About 10 g of each of three lactic acid-glycolic acid copolymers (ratio 75/25; average molecular weight 12,500) synthesized by different methods [i.e. (1) strongly anionic ion exchange resin catalyst method, (2) solid acid (acid clay) catalyst method and (3) catalystless method, each being a polycondensation method described below] was dissolved in about 20 ml of dichloromethane and the solution was poured into 1,000 ml of hot water at about 60° C. with stirring, whereby the dichloromethane was evaporated and the high molecular polymer came up to the surface. The latter was collected and dried under reduced pressure for drying and solvent removal to give the desired high molecular polymer. The polymer obtained was placed in a closed vessel and stored at room temperature. For stability evaluation, the thus stored sample was subjected to GPC (gel permeation chromatography) for average molecular weight determination. As shown by the results given in Table 1, marked improvement in stability was noted with the high molecular polymers obtained in accordance with the invention and having low free monomer acid contents.

TABLE 1

| Method of synthesis | | Lot. No. | Free acid content(*) | Average mol. wt. | | Initial inherent viscosity dl/g |
|---|---|---|---|---|---|---|
| | | | | Initial | After storage (months) at room temperature | |
| (1) | Control | 1-1 | 0.02 | 12,000 | (12) 4,400 | 0.14 |
| | Invention | 1-2 | 0.0033 | 11,900 | (12) 11,600 | 0.14 |
| (2) | Control | 2-1 | 0.0132 | 12,500 | (5) 4,100 | 0.15 |
| | Invention | 2-2 | 0.0033 | 12,500 | (5) 11,500 | 0.15 |
| (3) | Control | 3-1 | 0.0165 | 12,500 | (5) 5,800 | 0.15 |
| | Invention | 3-2 | 0.0055 | 12,500 | (5) 12,000 | 0.15 |

(*)Method of free acid determination: 300 mg of a sample is dissolved in 10 ml of dichloromethane, the solution is extracted with 20 ml of distilled water and 10 ml of the aqueous layer is titrated to neutral with 0.01 N NaOH (phenolphthalein indicator).
The values of free acid content given in Table 1 indicates the number of moles of free acids dissolved in water per 100 grams of the high molecular polymer as calculated on the assumption that said free acids each is a monobasic acid.

In preparing the lactic acid-glycolic acid copolymers used in the above, the following methods were used:
(1) Strongly anionic exchange resin catalyst method:
To 160 g of 85% aqueous lactic acid solution and 38 g of glycolic acid was added 6.8 g of Dowex 50W and the mixture was heated in a nitrogen atmosphere under reduced presure for 6 hours in a manner such that the inside temperature and pressure were initially 105° C. and 350 mmHg, respectively, and finally 150° C. and 30 mmHg, respectively, while removing the water distilled. Then, 6.8 g of Dowex 50W was added and the reaction was further carried out at 175° C. and 3-5 mmHg for 40 hours. While hot, the reaction mixture was filtered to thereby remove the Dowex 50W. The filtrate was cooled to give a lactic acid-glycolic acid copolymer.
(2) Solid acid (acid clay) catalyst method:
To 160 g of 85% aqueous lactic acid solution and 38 g of glycolic acid was added 17.4 g of acid clay and the mixture was heated in a nitrogen atmosphere for 6 hours while increasing the temperature and degree of pressure reduction stepwise in a manner such that the inside temperature and pressure were initially 105° C. and 350 mmHg, respectively, and finally 150° C. and 30 mmHg, respectively and while removing the water distilled. Thereafter, the inside pressure was reduced to 3 mmHg and heating was conducted for 36 hours while maintaining the inside temperature at 175° C. The reaction mixture was cooled to room temperature, 400 ml of methylene chloride was added, the resulting mixture was stirred for dissolution of the polymerization product, the acid clay was then filtered off, and the filtrate was concentrated to dryness to give a white lactic acid-glycolic acid copolymer.
(3) Catalystless method:
To 160 g of 85% aqueous lactic acid solution was added 38 g of glycolic acid and the mixture was heated in a nitrogen atmosphere under reduced pressure for 6 hours in a manner such that the inside temperature and pressure were initially 105° C. and 350 mmHg, respectively, and finally 150° C. and 30 mmHg, respectively, while removing the water distilled. Heating under reduced pressure was further conducted at 3-5 mmHg and 175° C. for 36 hours. Upon cooling to room temperature, there was obtained a colorless lactic acid-glycolic acid copolymer.

REFERENCE EXAMPLE

In 800 mg of distilled water were dissolved with warming 450 mg of leuprolide [the acetate of a polypeptide having the formula (Pyr)Glu-His-Trp-Ser-Tyr-D-Leu-Leu-Arg-Pro-NH-CH$_2$CH$_3$ and having luteinizing hormone releasing hormone (LH-RH)-like activity, wherein the abbreviations according to the IUPAC-IUB Commission on Bio-chemical Nomenclature are used, the amino acids, unless otherwise specified, being in the L form] and 40 mg of gelatin (internal water phase). Separately, 3.5 g of each of the lactic acid-glycolic acid copolymers of Reference Example 1, Lot Nos. 2-1, 2-2, 3-1 and 3-3, was dissolved in 5 ml of methylene chloride (oil phase). The oil phase was added to the water phase with stirring using Polytron (Kinematica, Switzerland) to give a w/o emulsion. The viscosity at 15° C. of the w/o emulsions derived from Lot No. 2-2 and No. 3-2 was 2,000. Separately, 200 ml of a 0.5% aqueous solution of polyvinyl alcohol was prepared. To this was added the w/o emulsiuon with stirring using Autohomomixer (Tokushu Kika, Japan), whereby a (w/o)/w emulsion was produced.

This emulsion was stirred with a propeller in a nitrogen stream for about 2 hours to thereby evaporate dichloromethane and to solidify the oil phase. The thus-formed microcapsules were collected by filtration, rinsed with water and dried. In 2 ml of dichloromethane and 7 ml of distilled water were dissolved 50 mg of the microcapsules obtained in the powder form, and the leuprolide concentration in the distilled water was determined by reversed-phase HPLC and the content of leuprolide incorporated into the microcapsules was calculated. Said content is given in Table 2 in terms of percentage to the theoretical content.

TABLE 2

| | Lot | Leuprolide content (%) |
|---|---|---|
| Invention | 2-2 | 95 |
| Invention | 3-2 | 97 |
| Control | 2-1 | 84 |
| Control | 3-1 | 64 |

As is evident from Table 2, the use of the high molecular polymers obtained by the method of the invention gave higher rates of leuprolide incorporation.

REFERENCE EXAMPLE 3

The microcapsules prepared in Reference Example 2 were weighed in 50-mg portions and each portion was dispersed in 10 ml of phosphate buffer (pH 7.0). The release of leuprolide from the microcapsules into the buffer was measured by stirring each dispersion at 25 rpm in a constant-temperature vessel maintained at 37° C.

With the leuprolide content as found in Reference Example 2 taken as the initial value, residual leuprolide percentages to the initial value were determined by subjecting the filtrates obtained after separation of microcapsules by filtration after storage at 37° C. for 1, 7, 14, 21 and 28 days to HPLC for determination of residual leuprolide. The percentage values thus obtained are shown in FIG. 1.

The data shown in FIG. 1 clearly indicate that the use of the high molecular polymers according to the present invention reduced the initial burst (release by one day) and allowed leuprolide release of approximately zero order over 1-1.5 months.

In FIG. 1, □ is for the high molecular polymer of Lot No. 2-1, ■ for the high molecular polymer of Lot No. 2-2, o for the high molecular polymer of Lot. No. 3-1 and ● for the high molelcular polymer of Lot No. 3-2.

REFERENCE EXAMPLE 4

A high molecular polymer was synthesized in the same manner as in Reference Example 1, method (3). The free acid content was found to be 0.021 mole per 100 g of the high molecular polymer obtained.

REFERENCE EXAMPLE 5

A high molecular polymer was produced by weighing 191 g of 85% aqueous lactic acid solution, 17.5 g of glycolic acid and 6.8 g of Dowex 50W and following the procedure of Reference Example 1, method (1). After removal of the water distilled, the reaction was performed at 3 mmHg and 175° C. for 72 hours. In this case, the free acid content was 0.018 mole per 100 g of the high molecular polymer obtained.

REFERENCE EXAMPLE 6

By following the procedure of Reference Example 1, method (3), 150 g of 85% aqueous lactic acid solution was treated and the water distilled was removed. Thereafter, the reaction was further conducted at 3 mmHg and 175° C. for 12 hours to give a high molecular polymer. In this case, the free acid content was 0.035 mole per 100 g of the high molecular polymer obtained.

EXAMPLE 1

The polylactic acid-glycolic acid obtained in Reference Example 4 by the catalystless method and having a lactic acid/glycolic acid ratio of 75/25 and an average molecular weight of 13,000 was dissolved in dichloromethane, and the solution was poured into hot water at about 60° C. with stirring, whereupon a high molecular polymer came up to the surface. This was collected and dried. The thus-obtained copolymer had a lactic acid/glycolic acid ratio of 75/25, a molecular weight of 13,000 and a free acid content of 0.005 mole per 100 g of the high molecular polymer. Its inherent viscosity was 0.15 as determined in chloroform at a concentration of 0.5%.

EXAMPLE 2

The polylactic acid-glycolic acid synthesized in Reference Example 5 using Dowex 50W as catalyst and having a lactic acid/glycolic acid ratio of 90/10 and an average molecular weight of 20,000 was dissolved in acetone, and the solution was poured into warm water at about 40° C., whereupon a high molecular polymer came up to the surface. The polymer was collected and dried. The copolymer thus obtained had a free acid content of 0.008 mole per 100 g of the high molecular polymer and an inherent viscosity of 0.48 as determined in chloroform at a concentration of 0.5%.

EXAMPLE 3

The polylactic acid synthesized in Reference Example 6 without catalyst and having an average molecular weight of 8,000 was finely pulverized and then treated in warm water at 50° C. for 20 minutes with stirring, followed by filtration and drying. The thus-obtained high molecular compound had a free acid content of 0.009 mole per 100 g thereof and an inherent viscosity of 0.10 as determined in chloroform.

EXAMPLE 4

The same high molecular polymer as used in Example 1 was rinsed in a 1:1 mixture of water and ethanol at 50° C. and then treated in the same manner as in Example 1. The high molecular polymer obtained had a free acid content of 0.0028 mole per 100 g of the high molecular polymer.

EXAMPLE 5

In dichloromethane (oil phase) 3 g of lactic acid-glycolic acid copolymer obtained in Reference Example 4 having lactic acid/glycolic acid ratio of 75/25 and an average molecular weight of 13,000 was dissolved. 60 mg of thyroid hormone releasing hormone tartarate (TRH-T) was dissolved in 800 mg of water (inner water phase).

The oil phase was added to the inner water phase with stirring using Polytron to give w/o emulsion. After cooling at 15° C., the w/o emulsiuon was added to 200 ml of 0.5% aqueous solution of polyvinyl alcohol, separately prepared and cooled at 15° C., with stirring using Autohomomixer to give (w/o)/w emulsion.

This emulsion was stirred with a propeller in a nitrogen stream for about 2 hours to thereby cause evaporation of the dichloromethane and solidification of the oil phase. The thus formed microcapsules were collected by filtration, rinsed with water and dried to form powder.

The "mole" used to show the weight amount of a compound is the abbreviation of "gram moles".

We claim:

1. A biodegradable high molecular polymer useful as an excipient in producing a pharmaceutical preparation comprising a copolymer or homopolymer of about 50–100 mole percent of lactic acid and about 50–0 mole percent of glycolic acid having a weight average molecular weight of about 2,000 to 50,000 and wherein the content of water-soluble low molecular compounds, as calculated on the assumption that each of said compounds is a monobasic acid, is less than 0.01 mole per 100 grams of said high molecular polymer.

2. The biodegradable high molecular polymer according to claim 1, wherein the high molecular polymer has an inherent viscosity of about 0.05–0.5 dl/g as determined with a 0.5 weight percent chloroform solution thereof and a weight average molecular weight of about 5,000–35,000.

3. A method of producing a biodegradable high molecular polymer according to claim 1, which method comprises removing by extraction of water-soluble low molecular compounds from a biodegradable high molecular polymer containing not less than 0.01 mole of water-soluble low molecular compounds per 100 grams thereof, as calculated on the assumption that each of said compounds is a monobasic acid, using water or a mixture of water and an organic solvent readily soluble in water.

4. The method according to claim 3 wherein the organic solvent readily soluble in water is a member selected from the group consisting of acetone, methanol, ethanol, tetrahydrofuran, acetonitrile and ethyl acetate.

5. The method according to claim 4, wherein the organic solvent readily soluble in water is ethanol.

6. The method according to claim 3, wherein a ratio of the mixture of water and organic solvent readily soluble in water (v/v) is about 100/0 to 100/100.

7. The method according ot claim 3, wherein the biodegradable high molecular polymer containing the water-soluble low molecular compounds is dissolved in advance in an organic solvent.

8. The method according to claim 3, wherein the removing by extraction of the water-soluble low molecular compounds is conducted under stirring.

9. The method according to claim 3, wherein the removing by extraction of the water-soluble low molecular compounds is conducted at a temperature of about 0° to 90° C.

10. The method according to claim 7, wherein the biodegradable high molecular polymer containing water-soluble low molecular compounds is dissolved in the 3 to 20 time amount (w/v) of an organic solvent, then the solution is poured into water under stirring at a temperature about 20° to 70° C. to remove the trace amount of water soluble low molecular compounds from the biodegradable high molecular polymer.

11. The biodegradable high molecular polymer according to claim 1, which is produced by removing by extraction of water-soluble low molecular compounds from a biodegradable high molecular polymer containing not less than 0.01 mole of water-soluble low molecular compounds per 100 grams thereof, as calculated on the assumption that each of said compounds is a monobasic acid, using water or a mixture of water and an organic solvent readily soluble in water.

* * * * *

(12) EX PARTE REEXAMINATION CERTIFICATE (5078th)
United States Patent
Yamamoto et al.

(10) Number: US 4,728,721 C1
(45) Certificate Issued: Mar. 8, 2005

(54) POLYMER, PRODUCTION AND USE THEREOF

(75) Inventors: Masaki Yamamoto, Osaka (JP);
Hiroaki Okada, Osaka (JP); Yasuaki Ogawa, Osaka (JP); Tsutomu Miyagawa, Saitama (JP)

(73) Assignees: Takeda Chemical Industries, Ltd., Osaka (JP); Wako Pure Chemical Industries, Ltd., Osaka (JP)

Reexamination Request:
No. 90/006,490, Dec. 20, 2002
No. 90/006,673, Jun. 23, 2003

Reexamination Certificate for:
Patent No.: 4,728,721
Issued: Mar. 1, 1988
Appl. No.: 06/858,040
Filed: May 1, 1986

(30) Foreign Application Priority Data

May 7, 1985 (JP) .............................. 60-97617

(51) Int. Cl.[7] ......................... C08G 63/90; C08G 63/08
(52) U.S. Cl. ....................... 528/361; 528/354; 528/499
(58) Field of Search ............................... 528/354, 361, 528/499

(56) References Cited

U.S. PATENT DOCUMENTS

| | | |
|---|---|---|
| 2,703,316 A | 3/1955 | Schneider |
| 3,043,782 A | 7/1962 | Jensen |
| 3,092,553 A | 6/1963 | Fisher, Jr. et al. |
| 3,523,906 A | 8/1970 | Vrancken et al. |
| 3,539,465 A | 11/1970 | Hiestand et al. |
| 3,565,869 A | 2/1971 | DeProspero |
| 3,636,956 A | 1/1972 | Schneider |
| 3,637,910 A | 1/1972 | Shima et al. |
| 3,691,090 A | 9/1972 | Kitajima et al. |
| 3,755,558 A | 8/1973 | Scribner |
| 3,773,919 A | 11/1973 | Boswell et al. ............... 424/19 |
| 3,839,297 A | 10/1974 | Wasserman et al. |
| 3,912,692 A | 10/1975 | Casey et al. |
| 3,922,338 A | 11/1975 | Estevenel et al. |
| 4,137,921 A | 2/1979 | Okuzumi et al. |
| 4,234,571 A | 11/1980 | Nestor et al. |
| 4,249,531 A | 2/1981 | Heller et al. |
| 4,273,920 A | 6/1981 | Nevin ........................ 528/361 |
| 4,384,975 A | 5/1983 | Fong |
| 4,389,330 A | 6/1983 | Tice et al. |
| 4,479,911 A | 10/1984 | Fong |
| 4,555,399 A | 11/1985 | Hsiao |
| 4,652,441 A | 3/1987 | Okada ........................ 424/19 |
| 4,675,144 A | 6/1987 | Hammond |
| 4,675,189 A | 6/1987 | Kent et al. |
| 4,677,191 A | 6/1987 | Tanaka et al. |
| 4,728,721 A | 3/1988 | Yamamoto et al. |
| 4,767,628 A * | 8/1988 | Hutchinson ................. 424/426 |
| 4,849,228 A | 7/1989 | Yamamoto et al. |
| 4,917,893 A | 4/1990 | Okada et al. |
| 4,954,298 A | 9/1990 | Yamamoto et al. |
| 5,330,767 A | 7/1994 | Yamamoto et al. |
| 5,476,663 A | 12/1995 | Okada et al. |
| 5,631,020 A | 5/1997 | Okada et al. |
| 5,631,021 A | 5/1997 | Okada et al. |
| 5,922,338 A | 7/1999 | Brich et al. |
| 5,945,126 A | 8/1999 | Thanoo et al. |
| 6,270,802 B1 | 8/2001 | Thanoo et al. |
| 6,565,874 B1 * | 5/2003 | Dunn et al. ................. 424/426 |

FOREIGN PATENT DOCUMENTS

| | | |
|---|---|---|
| CA | 1 169 090 | 6/1984 |
| EP | 052510 | 5/1982 |
| EP | 0052510 | 5/1982 |
| EP | 058481 | 8/1982 |
| EP | 0 058 481 B2 | 8/1982 |
| EP | 0 107 591 B2 | 5/1984 |
| EP | 0 145 240 B1 | 6/1985 |
| EP | 058 481 B1 | 10/1986 |
| FR | 2 126 270 | 10/1972 |
| FR | 2 491 351 | 4/1982 |
| FR | 2 551 072 | 3/1985 |
| GB | 929 402 | 6/1963 |
| GB | 2 088 314 A | 6/1982 |
| GB | 2145422 | 3/1985 |
| GB | 2 145 422 A | 3/1985 |
| JP | 43-3017 | 2/1943 |
| JP | 60-97617 | 5/1985 |

OTHER PUBLICATIONS

European File History, EP 86303417.9, pp. 18–53.
Chemical Engineer's Handbook, 5th Ed., Ch. 3 and 15, Robert H. Perry, ed., McGraw–Hill Book Co., NY.
Material Safety Data Sheet, "Methanol. Synthetic", Carolina Biological Supply Co., Burlington, NC.
Material Safety Data Sheet, "Methanol. 70%", Carolina Biological Supply Co., Burlington, NC.
Sales Specification, "Methanol, Premium Grade," Celanese Chemicals, Dallas, TX.
Sales Specification, "Methanol, Technical Grade," Celanese Chemicals, Dallas, TX.
Sales Specification, "Methanol, ACS Grade," Celanese Chemicals, Dallas, TX.
Vert, Michel et al., Makromol. Chem., Suppl. 5, 30–41 (1981).
Litigation transcript Tap Pharmact'l Prdts. et al v. OWL Pharmact'l, et al, pp. 744–51 (Nov. 26, 2002).
Transcript of Proceedings Before the Honorable Solomon Oliver, Jr., United States District Judge; United States District Court, Northern District of Ohio, Eastern Division, Tap Pharmaceutical Products, Inc., et al. vs. Owl Pharmaceuticals, L. L. C., et al., Case No. 1: 99CV2715, vols. I–IX (Transcript pp. 1–1115) including Jury Verdict Form (four pages).

(List continued on next page.)

*Primary Examiner*—P. Hampton Hightower

(57) ABSTRACT

The present invention provides a biodegradable high molecular polymer characterized in that the content of water-soluble low molecular compounds, as calculated on the assumption that said compounds each is a monobasic acid, is less than 0.01 mole per 100 grams of said high molecular polymer.

The thus-obtained molecular polymer has good aging stability and can be used advantageously as an excipient for pharmaceutical preparations.

OTHER PUBLICATIONS

A. Schindler, et al., "Biodegradable Polymers for Sustained Drug Delivery," *Contemporary Topics in Polymer Science,* vol. 2, pp. 251–289.
R.K. Kulkarni et al., "Biodegradable Poly(lactic acid) Polymer," *J. Biomed, Mater, Res.,* vol. 5, pp. 169–181 (1971).
Takeda Chemical v. Oakwood Lab., N. Dist. Ohio, 1:99–CV–2715, Court Order, Sept. 4, 2002, on Claim Construction and Infringement (16 pages).
Takeda Chemical v. Oakwood Lab., N. Dist. Ohio, 1:99–CV–2715, Defendants' Memorandum in Support of their Post–Trial Motions including Exhibits A–P, Dec. 6, 2002.
Takeda Chemical v. Oakwood Lab., N. Dist. Ohio, 1:99–CV–2715, Plaintiffs' Opposition to Defendants' Combined Motion for Judgment as a Matter of Law, including 14 Exhibits, Jan. 10, 2003.
Takeda Chemical v. Oakwood Lab., N. Dist. Ohio, 1:99–CV–15, Defendants' Reply Memorandum, Jan. 31, 2003 (no exhibits).
Pitt, Colin G. et al., "The Enzymatic Surface Erosion of Aliphatic Polyesters," *Journal of Controlled Release* 1 (1984), pp. 3–14, the month in the date of publication is not available.
Pitt et al., "Aliphatic Polyesters. I. The Degradation of Poly (e–caprolactone) In Vivo," *Journal of Applied Polymer Science,* vol. 26 (1981) pp. 3779–3787.
Microcapsule, Industrial Technology Library 25, pp. 102–103 (1971).
*Journal of the Chemical Society of Japan,* vol. 72, 1969, pp. 493–499.
*The Pharmacopoeia of Japan,* Tenth Ed., 1982, pp. 16–21.
Chang, "Biodegradable Semipermeable Microcapsules Containing Enzymes, Hormones, Vaccines and Other Biologicals," *J. of Bioengineering,* vol. 1:25–32 (1976).
Lachman et al., *The Theory and Practice of Industrial Pharmacy,* Lea & Febiger, Philadelphia, 1970, pp. 384–391.
European Search Report, European Patent Appln. No. 86300308.
Ogawa et al., "Controlled Release of LHRH Agonist, Leuprolide Acetate, from Microcapsules: Serum Drug Level Profiles and Pharmacological Effects in Animals," *J. Pharm. Pharmacol.* 1989, 41: 439–440.
Sanders et al., "Controlled Release of a Luteinizing Hormone–Releasing Hormone Analogue from Poly(d, l–lactide–co–glycolide) Microspheres," *Journal of Pharmaceutical Sciences,* vol. 73, No. 9, Sep. 1984.
Keipert et al., "Antiglaumakotosahaltige Ophthalmika mit Prolongierter Wirkung auf Basis Makromiekularer Hilfsstoffe, Teil 3," *Die Pharmazie,* vol. 45, No. 8, pp. 594–595 (Jul. 1990).
Asahara, "Production of Polyglycolide Lactide and Properties of the Product," *J. Chem. Soc. Japan,* 65 (1965), No. 5, pp. 983–986.
Omelczuk et al., "The Influence of Polymer Glass Transition Temperature and Molecular Weight on Drug Release from Tablets Containing Poly(DL–lactic Acid)," *Pharmaceutical Research,* vol. 9, No. 1, Jan. 1992.
Omelczuk et al., "Effect of Thermal Treatment on the Physical Mechanical and Dissolution Properties of Compacts Containing Biodegradable Polymers," *Proceedings of the Ninth International Conference,* Veldhoven, The Netherlands, vol. 1, pp. 28–44 (1990).
Arshady, "Preparation of biodegradable microspheres and microcapsules: 2. Polylactides and related polyesters," *Journal of Controlled Release,* vol. 17, pp. 1–22 (1991).
Sato et al., "Porous Biodegradable Microspheres for Controlled Drug Deliver. I. Assessment of Processing Conditions and Solvent Removal Techniques," *Pharm. Res.,* vol. 5, No. 1, pp. 21–30 (1988).
Rothen–Weinhold et al., "Analysis of the influence of polymer characteristics and core loading on the in vivo release of a somatostatin analogue," *European Journal of Pharmaceutical Sciences,* vol. 5 (1997), pp. 303–313.
Bodmeier et al., "The effect of the addition of low molecular weight poly (DL–lactide) on drug release from biodegradable poly (DL–lactide) drug delivery systems," *International Journal of Pharmaceutics,* vol. 51 (1989), pp. 1–8.
Johnson et al., "The Stabilization and Encapsulation of Human Growth Hormone into Biodegradable Microspheres," *Pharmaceutical Research,* vol. 14, No. 6, 1997.
Vert et al., "Something new in the field of PLA/GA bioresorbable polymers?" *Journal of Controlled Release,* vol. 53, (1998), pp. 85–92.
Okada, "One– and three–month release injectable microspheres of the LH–RH superagonist leuprorelin acetate," *Elsevier Science B.V.* (1997), pp. 43–70.
File History of U.S. Patent No. 4,728,721, Mar. 1, 1988, Masaki Yamamoto et al.
File History of U.S. Patent No. 4,849,228, Jul. 18, 1989, Application No. 117618.
Takeda Chemical v. Oakwood Lab., N. Dist. Ohio, 1:99–CV–2715, Proposed Joint Trial Stipulations.
Letter to the European Patent Office from Elkington and Fife dated Apr. 23, 1990.
R.K. Kulkarni et al., "Biodegradable Poly(lactic acid) Polymers," pp. 169–181 (1971).
Communication from the European Patent Office pursuant to Article 96(2) and Rule 51(2) EPC (EP 86 303 417.9).
European Patent Application 0 202 065 A2, Nov. 20, 1986, Masaki Yamamoto et al.
A. Schindler et al., "Biodegradable Polymers for Sustained Drug Delivery," *Contemporary Topics in Polymer Science,* vol. 2, pp. 251–285 (1977).
European Patent Application 0 052 510, Publication Date May 26, 1982.
E. David Crawford et al., "Total Androgen Ablation: American Experience," *The Urologic Clinics of North America,* Feb. 1991, pp. 55–63, vol. 18, No. 1.
Copy of the cover of a certified copy of Patent Application No. 86303417.9.
Roland Bodmeier et al., "The Preparation and Evaluation of Drug–Containing Poly (dl–lactide) Microspheres Formed by the Solvent Evaporation Method," *Pharmaceutical Research,* 1987, pp. 465–471, vol. 4, No. 6.
Curt Thies and Marie–Christine Bissery, "Biodegradable Microspheres for Parenteral Administration," *Biomedical Applications of Microencapsulation,* Chapter 3, pp. 53–74 (1984).
A. Schindler et al., Biodegradable Polymers for Sustained Drug Delivery, *Contemporary Topics in Polymer Science,* vol. 2, pp. 251–85 (1977).
Instructions on How to Mix and Administer Leupron Depot (Dec. 2000).
Zoladex 3.6 mg (2001).

Rahul C. Mehta et al., "Peptide containing microspheres from low molecular weight and hydrophilic poly(d.l–lactide–co–glycolide)," *Journal of Controlled Release,* 1996, pp. 249–257.

William W. Scott, Historical Overview of the Treatment of Prostatic Cancer, *The Prostate,* 1983, pp. 435–440, vol. 4.

Rooholla Sharifi et al., "Therapeutic effects of leuprorelin microspheres in prostate cancer," *Advanced Drug Delivery Reviews,* 1997, pp. 121–138.

R.K. Kulkani, Ph.D., et al., "Polylactic Acid for Surgical Implants," *Archives of Surgery,* Nov. 1966, pp. 839–843, vol. 93, No. 5.

Facsimile dated Aug. 12, 1991, to European Patent Office regarding European Patent Application No. 86 303 417.9 referring to ourstanding Official Communication of Feb. 8, 1991.

Provision of a copy of the minutes in accordance with Rule 76(4) EPC in EP application No. 86 303 417.9.

Schindler et al; "Biodegradable Polymers for Sustained Drug Delivery"; *Contemporary Topics in Polymer Science,* pp. 251–289 (1977).

Vert et al; "Stereoregular Bioresorbable Polyesters for Orthopedic Surgery"; *Makro Mol. Chem. Suppl. 5,* pp. 30–41 (1981).

Kulkarni et al; "Biodegradable Poly (lactic acid) Polymers", *J. BioMed. Mater. Res.,* pp. 169–181 (1971).

European Patent Application 86303417.9, equivalent to the application resulting in th '721 patent.

EPO Office Action date Jan. 15, 1990 from prosecution of EPO Application 86303417.9.

Patentee's response dated Apr. 23, 1990 from prosecution of EPO Application 86303417.9.

EPO Office Action dated Feb. 8, 1991 from prosecution of EPO Application 86303417.9.

Patentee's response dated Aug. 12, 1991 from prosecution of EPO Application 86303417.9.

European Patent 0202065, equivalent to the '721 patent.

Trial transcript excerpts from testimony of inventor Ogawa in Case No. 1:99 CV 2715, TAP v. OWL; Northern District of Ohio.

Trial transcript excerpts from testimony of patentee's expert Storey in Case No. 1:99 CV 2715, TAP v. OWL; Northern District of Ohio.

The Merck Index Eleventh Edition, pp. 707 and 842 (1989).

'Orange Book' listing for Lupron.

Summary of prosecution history of the European equivalent to the '721 patent.

Summary of patentee admissions during the '721 litigation.

* cited by examiner

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–11 is confirmed.

* * * * *